(12) United States Patent
Maier

(10) Patent No.: US 10,251,840 B2
(45) Date of Patent: Apr. 9, 2019

(54) METHOD FOR MANUFACTURING ACID PELLETS

(71) Applicant: Johann-Georg Maier, Bingen (DE)

(72) Inventor: Johann-Georg Maier, Bingen (DE)

(73) Assignee: Boehringer Ingelheim International GmbH, Ingelheim am Rhein (DE)

(*) Notice: Subject to any disclaimer, the term of this patent is extended or adjusted under 35 U.S.C. 154(b) by 1019 days.

(21) Appl. No.: 13/938,402

(22) Filed: Jul. 10, 2013

(65) Prior Publication Data

US 2013/0295189 A1   Nov. 7, 2013

Related U.S. Application Data

(63) Continuation of application No. 12/934,828, filed as application No. PCT/EP2009/053468 on Mar. 24, 2009, now abandoned.

(30) Foreign Application Priority Data

Mar. 28, 2008 (EP) .................... 08153668

(51) Int. Cl.
| | |
|---|---|
| *A61K 9/14* | (2006.01) |
| *A61K 9/50* | (2006.01) |
| *A61K 31/4184* | (2006.01) |
| *A61K 31/4439* | (2006.01) |
| *A61K 31/519* | (2006.01) |
| *A61K 31/60* | (2006.01) |
| *B05D 5/00* | (2006.01) |

(52) U.S. Cl.
CPC ............ *A61K 9/146* (2013.01); *A61K 9/5078* (2013.01); *A61K 31/4184* (2013.01); *A61K 31/4439* (2013.01); *A61K 31/519* (2013.01); *A61K 31/60* (2013.01); *B05D 5/00* (2013.01)

(58) Field of Classification Search
CPC .......... A61K 9/14; A61K 9/145; A61K 9/146; A61K 9/16; A61K 9/1605; A61K 9/1652; A61K 9/167; A61K 9/1676; A61K 9/1682
See application file for complete search history.

(56) References Cited

U.S. PATENT DOCUMENTS

| | | | |
|---|---|---|---|
| 4,684,516 A * | 8/1987 | Bhutani | A61J 3/10 264/109 |
| 6,015,577 A | 1/2000 | Eisert et al. | |
| 6,284,271 B1 | 9/2001 | Lundberg et al. | |
| 6,663,901 B1 | 12/2003 | Gilis et al. | |
| 2003/0181488 A1 | 9/2003 | Brauns | |
| 2006/0183779 A1 | 8/2006 | Brauns et al. | |

FOREIGN PATENT DOCUMENTS

| | | | |
|---|---|---|---|
| CA | 1302272 C | 6/1992 | |
| CA | 2476054 A1 | 9/2003 | |
| EP | 257344 A1 | 3/1988 | |
| EP | 1894561 A1 * | 3/2008 | ........... A61K 9/5078 |
| EP | 1894561 A1 * | 3/2008 | ........... A61K 9/5078 |
| WO | 2003074056 A1 | 9/2003 | |
| WO | 2008009639 A2 | 1/2008 | |
| WO | 2008022932 A2 | 2/2008 | |
| WO | WO 2008022932 A2 * | 2/2008 | ........... A61K 9/5073 |
| WO | WO-2008022932 A2 * | 2/2008 | ........... A61K 9/5073 |

OTHER PUBLICATIONS

International Search Report, PCT/EP2009/053468, dated May 25, 2009.
Luo, et al., "Dry coating, a novel coating technology for pharmaceutical dosage forms", International Journal of Pharmaceutics, vol. 358, No. 1-2, 2008, p. 16-22.

* cited by examiner

*Primary Examiner* — Micah Paul Young
(74) *Attorney, Agent, or Firm* — Philip I. Datlow

(57) ABSTRACT

The invention relates to an improved method of manufacturing substantially spherical/ball-shaped tartaric acid starter pellets which are suitable for preparing active substance-containing medicament formulations, as well as the pellets as such that may be obtained in this way, and their use as starting material for the preparation of active substance-containing medicament formulations.

7 Claims, No Drawings

METHOD FOR MANUFACTURING ACID PELLETS

This application is a continuation of co-pending application Ser. No. 12/934,828, filed on Sep. 27, 2010, which is the national phase entry under 35 U.S.C. § 371 of International Application No. PCT/EP2009/053468, filed Mar. 24, 2009, which claims priority to European Patent Application No. 08153668.2, filed Mar. 28, 2008, the contents of which are hereby incorporated by reference in their entireties.

The invention relates to an improved method of manufacturing substantially spherical/ball-shaped tartaric acid starter pellets which are suitable for preparing active substance-containing medicament formulations, as well as the pellets as such that may be obtained in this way, and their use as starting material for the preparation of active substance-containing medicament formulations.

BACKGROUND TO THE INVENTION

Pellets, i.e. small round spherules, are known from the prior art as the basis for pharmaceutical formulations. Often, so-called "neutral" pellets consisting of maize starch and sucrose are used as the basis for pharmaceutical formulations in pellet form. It is also possible to use starter pellets which consist predominantly of an organic acid. A pellet formulation of this kind is disclosed for example in WO 03/074056. These formulations are compositions in which a layer of active substance which contains binder and optionally parting compounds is applied to a substantially spherical core material which consists of or contains the pharmaceutically acceptable organic acid, so as to enclose the core material. The core layer and the active substance layer are separated from one another by a so-called insulating layer. The structure of an active substance formulation of this kind is shown schematically in FIG. 1 of WO 03/074056.

The production of acid starter pellets of this kind with the required substantially spherical geometry has, however, proved unexpectedly difficult. In particular, there is always the possibility of excessive deviations from the desired spherical symmetry, for example with clumps formed by a larger sphere with smaller clumps adhering to the outside, forming so-called satellites. In pellet formulations in which the starter pellet is surrounded by an acid-sensitive active substance layer, these satellites may break off after the application of the insulating layer and thus give rise to defects in the insulation. This in turn has a detrimental effect on the storage stability of the active substance pellets.

The problem of the present invention is to provide so-called starter pellets which have a uniform, sphere-like geometry. In addition, they should have only a small number of potential defects in the insulation caused by satellites. It is particularly important to achieve as perfectly spherical a shape as possible and a low surface roughness for acid-sensitive active substances, where defects in the insulation caused by broken off satellites or by an excessively rough surface on over-sized particles of tartaric acid powder can lead to a significantly impaired storage stability and hence shelf life of the finished product. For this reason, with acid-sensitive active substances, it is also essential to apply the insulating layer as such with high reproducibility and a consistently high quality.

DETAILED DESCRIPTION OF THE INVENTION

The present invention relates to a method for manufacturing starter pellets which solve the problem outlined above.

The process according to the invention is characterised by a series of partial steps. First, the core 1 is produced from pharmaceutically acceptable organic acid. Within the scope of the present invention tartaric acid is used to prepare the core 1. The core material 1 thus obtained is then converted into so-called insulated tartaric acid cores 3 by spraying on an insulating suspension 2. Within the scope of the present invention, the insulated tartaric acid cores 3 may optionally also be referred to as insulated tartaric acid pellets 3 or as starter pellets.

The core 1 is prepared from tartaric acid particles with a particle size in the range from 0.2-0.8 mm, preferably 0.3-0.7 mm, particularly preferably 0.4-0.6 mm (determined by air jet screening) onto which a solution of tartaric acid and binder is sprayed. The following method is used to prepare the solution. Tartaric acid is first of all dissolved in water together with a suitable binder, preferably with acacia (gum arabic) at elevated temperature, preferably at a temperature in the range from 30-70° C., particularly preferably in the range from 40-60° C. Preferably, 0.1-0.3 kg, particularly preferably 0.15-0.25 kg, particularly about 0.2 kg acacia are used per kilogram of tartaric acid put in. The amount of water is preferably 0.6-1.0 kg, preferably 0.7-0.9 kg, particularly about 0.8 kg per kilogram of tartaric acid put in.

Preferably, according to the invention, first of all a clear solution of acacia in water is prepared at the above-mentioned temperature. Once this has been obtained, the tartaric acid is then added preferably at constant temperature and while stirring continues. After the addition has ended the mixture is stirred for at least 1 hour, preferably between 3 and 10, particularly preferably 4-8, particularly preferably 5-6 hours.

The solution thus obtained is sprayed onto tartaric acid particles with a particle size of 0.2-0.8 mm, preferably 0.3-0.7 mm, particularly preferably 0.4-0.6 mm. The proportion of particles with the above-mentioned particle size should be at least 90%, preferably at least 95%, particularly preferably at least 97%. For this, the tartaric acid particles are placed in a suitable container. The container is preferably a pan in which the particles are mixed and moved about by the rotation of the pan. Various designs of pan are known in the art and may optionally also be referred to as drum coaters. On this subject reference is made for example to the disclosures of EP 80199, WO 83/03052, WO 95/19713 or WO 06/134133. Within the scope of the present invention pans that may be used in the process according to the invention are optionally also known as horizontal pans.

The acid gum solution prepared by the method described hereinbefore is then sprayed onto the particles kept moving by rotation.

Within the scope of the present invention the material supplied for spraying is optionally also referred to as the pellet bed. The term pellet is to be regarded as equivalent to the term particle or core within the scope of the present invention.

According to the invention, preferably 0.8-1.6 kg, particularly preferably 1.0-1.4 kg, particularly preferably 1.2 kg of the above-mentioned acid gum solution are sprayed on per kilogram of tartaric acid particles supplied.

The amount of supply air in the process according to the invention is dependent on the batch size. The standardised amount of supply air per kilogram of tartaric acid cores supplied according to the invention is preferably in the range from 0.5-2 $(m^3/h)/kg$, preferably 0.75-1.5 $(m^3/h)/kg$, particularly preferably 0.9-1.1 $(m^3/h)/kg$. By the amount of supply air is meant the amount of dry air introduced into the rotating pellet bed per hour. If for example 1000 kg tartaric acid cores are placed in one batch, a standardised amount of supply air of 1.0 (m³/h)/kg corresponds to an actual amount of supply air of 1000 m³/h. The temperature of the supply air fed in for drying according to the invention is preferably below 90° C., particularly preferably below 80° C. Ideally the temperature of the supply air should be in the range from 35°-75° C.

The pellet temperature (the temperature of the pellet bed formed) according to the invention is preferably in the range from 30-50° C., particularly preferably 36-44° C., ideally 38-42 ° C.

The differential pressure is preferably 1-3 mbar, particularly preferably 1.5-2.5 mbar, particularly preferably 1.8-2.2 mbar. The differential pressure is the pressure difference between the pan pressure and ambient pressure. The pan should preferably be at reduced pressure so that no acid dust escapes.

Spraying is carried out at a defined spray rate. By the spray rate is meant the amount of acid gum solution that is sprayed onto the rotating pellet bed per hour. The spray rate is dependant on the batch size in the process according to the invention. The standardised spray rate according to the invention per kilogram of tartaric acid crystals supplied is preferably in the range from 0.2-0.4 (kg/h)/kg, preferably 0.25-0.35 (kg/h)/kg, particularly preferably 0.28-0.32 (kg/h)/kg. If for example 1000 kg tartaric acid crystals are placed in one batch, a standardised spray rate of 0.3 (kg/h)/kg corresponds to an actual spray rate of 300 kg/h.

After a first portion of the acid gum solution has been sprayed onto the tartaric acid particles of particle size 0.2-0.8 mm and the solution has been distributed by rotating the pan, fine tartaric acid powder is sprinkled onto the moist tartaric acid particles. This tartaric acid powder consists of fine tartaric acid particles with a particle size of <100, preferably <75, particularly preferably <50 microns (determined by air jet screening). The proportion of particles with the above-mentioned particle size should be at least 85%, preferably at least 90%, particularly preferably at least 94%. According to the invention preferably 0.4-1.2 kg, particularly preferably 0.6-1.0 kg, particularly preferably 0.8 kg of the above-mentioned tartaric acid powder are used per kilogram of tartaric acid particles supplied. After sprinkling with the above-mentioned tartaric acid powder the material for spraying is dried until a product temperature of about 30-50° C., preferably about 40° C. is reached. After this, the acid gum solution is sprayed on again.

To ensure the uniform formation of spherical particles, the spraying on of the acid gum solution and the sprinkling with tartaric acid powder are carried out alternately. The total amounts of acid gum solution and tartaric acid powder are supplied in at least 100, preferably 150 to 350, particularly preferably 200 to 300, particularly preferably about 250 batches of similar size and the process steps described hereinbefore are repeated a corresponding number of times.

Once the process has ended, the cores 1 obtained are dried. The drying is preferably carried out at a temperature of 50-70° C., preferably 55-65° C. over a period of 24-72 hours, preferably 36-60 hours.

After the preparation of the tartaric acid cores 1 so-called insulation of the core material is necessary. An insulating layer is applied around the tartaric acid core, preventing any interaction of active substance with tartaric acid core in the later product.

The core material is insulated by spraying an insulating suspension 2 onto the tartaric acid cores 1 obtained by the process described hereinbefore. To prepare the insulating suspension 2 ethanol is placed in the batch container and hydroxypropylmethylcellulose and dimethylpolysiloxane are added and dissolved therein with stirring, then talc is added and suspended.

The use of hydroxypropylmethylcellulose and talc has proved superior to the use of gum arabic and talc, for example. By using hydroxypropylmethylcellulose together with talc it is possible to produce an insulating layer of constant quality in a reproducible manner. This quality and reproducibility has been tested on an industrial scale.

To prepare the insulating suspension 2, preferably 0.04-0.06 kg, particularly preferably 0.046-0.05 kg hydroxypropylmethylcellulose are used per kilogram of ethanol. Besides the use of hydroxypropylmethylcellulose it has proved particularly preferable according to the invention to add dimethylpolysiloxane to the insulating suspension 2 to prevent foaming. The amount of dimethylpolysiloxane which is added with stirring to the preparation of the insulating suspension 2 is preferably 0.6-1.2 g, particularly preferably 0.8-0.9 g per kilogram of ethanol. Finally talc is added and suspended therein with stirring. Preferably 0.04-0.06 kg, particularly preferably 0.046-0.05 kg talc are used per kilogram of ethanol.

In one aspect the present invention relates to an ethanolic insulating suspension 2 which contains hydroxypropylmethylcellulose, preferably in the amounts stated above. In another aspect the present invention relates to an ethanolic insulating suspension 2 which contains, in addition to hydroxypropylmethylcellulose, dimethylpolysiloxane, preferably in the amounts stated above. In another aspect the present invention relates to an ethanolic insulating suspension 2 which also contains, in addition to hydroxypropylmethylcellulose and dimethylpolysiloxane, talc, preferably in the amounts stated above. In another aspect the present invention relates to an ethanolic insulating suspension 2 which may be obtained according to the method described hereinbefore.

In another aspect the present invention relates to the use of the ethanolic insulating suspension 2 for insulating tartaric acid cores 1. In another aspect the present invention relates to the use of the ethanolic insulating suspension 2 as a starting material for the preparation of a medicament formulation of dabigatran etexilate methanesulphonate.

The insulating suspension 2 thus prepared is sprayed onto the previously prepared tartaric acid pellets 1 in a continuous spray process in a conventional horizontal coater. 0.5-0.8 kg, preferably 0.55-0.75 kg, particularly preferably 0.6-0.7 kg of insulating suspension are sprayed on per kilogram of tartaric acid cores 1 supplied.

The spraying is carried out at a defined spray rate. By the spray rate is meant the amount of insulating suspension 2 sprayed onto the pellets 1 per hour. The spray rate in the process according to the invention is dependent on the batch size. The standardised spray rate according to the invention is preferably in the range from 0.01-0.1 (kg/h)/kg, preferably 0.02-0.04 (kg/h)/kg, particularly preferably 0.025-0.035 (kg/h)/kg per kilogram of tartaric acid pellets 1 supplied. If for example 1200 kg tartaric acid cores are placed in one batch, a standardised spray rate of 0.027 (kg/h)/kg corresponds to an actual spray rate of 32 kg/h. If for example 600 kg tartaric acid cores are placed in one batch, a standardised spray rate of 0.035 (kg/h)/kg corresponds to an actual spray rate of 21 kg/h.

During this continuous process the cores are dried continuously with a supply of air at up to 70° C., preferably from 25-70° C.

By the amount of supply air is meant the amount of dry air that is introduced into the rotating pellet bed per hour. The amount of supply air in the process according to the invention is dependant on the batch size. The standardised amount of supply air according to the invention is preferably in the range from 1.0-2.5 (m$^3$/h)/kg, preferably 1.2-2.0 (m$^3$/h)/kg, particularly preferably 1.40-1.85 (m$^3$/h)/kg per kilogram of tartaric acid cores 2 originally supplied. If for example 600 kg tartaric acid cores 2 are placed in one batch, a standardised amount of supply air of 1.83 (m$^3$/h)/kg corresponds to an actual amount of supply air of 1100 m$^3$/h. If for example 1200 kg tartaric acid cores 3 are placed in one batch, a standardised amount of supply air of 1.42 (m$^3$/h)/kg corresponds to an actual amount of supply air of 1700 m$^3$/h.

In another aspect the present invention relates to the insulated tartaric acid cores 3 per se which are obtained by the above method.

The insulated tartaric acid cores 3 which may be obtained according to the invention have a uniform, sphere-like geometry that makes further processing considerably easier. In addition, the pellets 3 according to the invention have only minor defects caused by so-called satellites. So-called satellites were small particles adhering to the outside of the otherwise rounded pellets, which have an adverse effect on the otherwise sphere-like geometry of the pellets. It is particularly important to achieve as perfectly spherical a shape as possible and a low surface roughness of the pellets 3 for acid-sensitive active substances, where defects in the insulating layer caused by satellites or an excessively rough surface caused by oversize particles of tartaric acid powder might lead to a significant impairment in the storage stability and hence the shelf life of the finished product.

Pellets containing active substance may be prepared from the pellets 3 according to the invention using methods described in the prior art.

In another aspect the present invention relates to the use of the pellets 3 according to the invention as starting material for preparing medicament formulations containing active substance.

Examples of the preparation of pellet formulations of dipyridamole starting from starter pellets may be found in EP32562 (particularly Examples 1 and 2). Examples of the preparation of pellet formulations of dipyridamole combined with acetylsalicylic acid may be found in EP257344 (cf. in particular Example 2). For the preparation of formulations containing dabigatran reference is made by way of example to the disclosure of WO 03/074056.

The methods of coating starter pellets with active substance described in the above-mentioned documents may also be used starting from the pellets 3 according to the invention.

In another aspect therefore the present invention relates to the use of the pellets 3 according to the invention as starting material for the preparation of active substance-containing medicament formulations in which the active substance is selected from among dipyridamole, dabigatran und acetylsalicylic acid or combinations thereof.

In a preferred aspect the present invention relates to the use of the pellets 3 according to the invention as starting material for the preparation of a dipyridamole-containing formulation. Another preferred aspect of the present invention relates to the use of the pellets 3 according to the invention as starting material for the preparation of a dabigatran-containing formulation.

The Examples that follow serve to illustrate the present invention in more detail.

Determining the Particle Sizes of Tartaric Acid by Air Jet Screening

Measuring Device and Settings:
Measuring device: Air jet screen, e.g. Alpine A 200 LS
Screens: As required
Weight put in: 10 g/screen
Duration: 1 min/screen, then 1 min each up to the maximum weight loss of 0.1 g Preparation of Sample/Supply of Product:

The substance is transferred into a mortar and any lumps present are destroyed by intensive pounding. The screen with rubber seal and cover is placed on a balance, set to zero and 10.0 g of the pounded substance are weighed onto the screen. The screen together with its contents, rubber seal and cover are placed on the device. The timer is set to 1 minute and the material is treated by air jet screening for this time. Then the residue is weighed out and documented. This process is repeated until the decrease in the weight of the residue after air jet screening is <0.1 g.

EXAMPLE 1

Preparation of the Starter Pellets 480 kg water are heated to 50° C. and 120 kg of acacia (gum arabic) are added with stirring in a conventional mixing container having a dished end and stirrer. Stirring is continued at constant temperature until a clear solution is obtained. Once there is a clear solution (usually after 1 to 2 hours) 600 kg tartaric acid are added with stirring. The tartaric acid is added at constant temperature while stirring is continued. After the addition has ended the mixture is stirred for about another 5 to 6 hours.

1000 kg tartaric acid are added to a slowly rotating (3 revolutions per minute) unperforated horizontal pan with a spraying and powder applying unit (e.g. Driamat 2000/2.5). Before spraying starts, a sample of the acid is taken for screening analysis. The acid in question is tartaric acid particles with a particle size in the range from 0.4-0.6 mm.

The acid gum solution obtained by the above method is sprayed onto the tartaric acid particles thus provided. During the spraying, the quantity of air supplied is adjusted to 1000 m$^3$/h and 35°-75° C. The differential pressure is 2 mbar and the speed of rotation of the pan is 9 revolutions per minute. The nozzles should be arranged at a distance of 350-450 mm from the filling.

The acid gum solution is sprayed on by alternating with the following steps. After about 4.8 kg of the acid gum solution has been sprayed onto the tartaric acid particles of particle size 0.4-0.6 mm and the solution has been distributed, about 3.2 kg tartaric acid powder are sprinkled onto the damp tartaric acid particles. The tartaric acid powder in question consists of fine tartaric acid particles with a particle size of <50 microns. In all, 800 kg tartaric acid powder are required. After the said tartaric acid powder has been sprinkled on and distributed the spray material is dried until a product temperature of about 40° C. is reached. This is in turn followed by the spraying on of the acid gum solution.

These cycles are repeated until the acid gum solution is used up. Once the process has ended the acid pellets are dried in the pan at 3 rpm for 240 minutes. To prevent caking after the drying has finished, an intermittent program is run at 3 rpm for 3 minutes every hour. In the present instance this means that the pan is rotated at 3 rpm for 3 minutes at intervals of one hour and then left to stand. The acid pellets are then transferred into a dryer. They are then dried at 60° C. over a period of 48 hours. Finally, the particle size distribution is determined by screen analysis. The particle size with a diameter of 0.6-0.8 mm corresponds to the product. This fraction should make up >85%.

EXAMPLE 2

Isolation of the Starter Pellets

To prepare the insulating suspension, 666.1 (347.5) kg of ethanol are placed in the mixing container and the hydroxypropylmethylcellulose (33.1 (17.3) kg) is added with stirring at approx. 600 rpm and dissolved. Then under the same conditions 0.6 (0.3) kg dimeticone are added. Shortly before use, talc (33.1 (17.3) kg) is added, again with stirring, and suspended.

The acid pellets 1200 (600) kg are poured into the coating apparatus (e.g. GS-Coater Mod. 600/Mod. 1200) and sprayed therein in the rotating pan with the insulating suspension described above in a continuous spraying process lasting several hours at a spraying rate of 32 kg/h for the 1200 kg mixture or 21 kg/h for the 600 kg mixture. The pellets are also dried continuously with an air supply at up to 70° C.

After the GS-Coater has been emptied, the insulated starter pellets are fractionated by screening. The product fraction with a diameter ≤1.0 mm is stored and used further.

The invention claimed is:

1. A method of preparing insulated tartaric acid pellets 3, comprising a first step of preparing tartaric acid pellets 1 comprising alternatively spraying tartaric acid particles with a solution of tartaric acid and a binder followed by sprinkling the tartaric acid particles with a fine tartaric acid powder having a particle size of <100 microns, wherein at least 90% of the tartaric acid particles have a particle size in the range from 0.4-0.6 mm, and in a second step, spraying an ethanolic insulating suspension 2 comprising hydroxypropylmethylcellulose onto the tartaric acid pellets 1 to form insulated tartaric acid pellets 3 having substantially uniform, sphere-like shapes.

2. The method of preparing insulated tartaric acid pellets 3 according to claim 1, wherein at least 85% of the fine tartaric acid powder has a particle size of <75 microns.

3. The method of preparing insulated tartaric acid pellets 3 according to claim 1, wherein the ethanolic insulating suspension 2 further comprises talc.

4. The method of preparing insulated tartaric acid pellets 3 according to claim 3 wherein the ethanolic insulating suspension 2 further comprises dimethylpolysiloxane.

5. Insulated tartaric acid pellets 3 made by the method according to claim 1.

6. A method for manufacturing an active substance-containing pharmaceutical formulation comprising applying an active substance to the insulated tartaric acid pellets 3 prepared in claim 1.

7. The method according to claim 6, wherein active substance is dipyridamole, dabigatran, acetylsalicylic acid or a combination thereof.

* * * * *